(12) United States Patent
Doostdar

(10) Patent No.: US 6,649,566 B2
(45) Date of Patent: Nov. 18, 2003

(54) STABILIZED CONCENTRATED FORMULATIONS FOR ENHANCING PLANT DEFENSIVE RESPONSES

(75) Inventor: Hamed Doostdar, Ft. Pierce, FL (US)

(73) Assignee: Morse Enterprises Limited, Inc., Miami, FL (US)

( * ) Notice: Subject to any disclaimer, the term of this patent is extended or adjusted under 35 U.S.C. 154(b) by 0 days.

(21) Appl. No.: 10/013,695

(22) Filed: Dec. 13, 2001

(65) Prior Publication Data

US 2003/0139295 A1 Jul. 24, 2003

(51) Int. Cl.$^7$ .......................... A01N 37/10; A01N 43/10
(52) U.S. Cl. ..................... 504/140; 504/144; 504/292; 504/324
(58) Field of Search ................................. 504/140, 144, 504/324, 292

(56) References Cited

U.S. PATENT DOCUMENTS

| | | | |
|---|---|---|---|
| 4,988,729 A | 1/1991 | Krämer et al. |
| 4,988,819 A | 1/1991 | Stroech et al. |
| 4,990,677 A | 2/1991 | Stroech et al. |
| 5,057,143 A | 10/1991 | Rheinheimer et al. |
| 5,085,686 A | 2/1992 | Vogelbacher et al. |
| 5,185,027 A | 2/1993 | Vogelbacher et al. |
| 5,308,828 A | 5/1994 | Eicken et al. |
| 5,360,913 A | 11/1994 | Rheinheimer et al. |
| 5,362,876 A | 11/1994 | Eicken et al. |
| 5,783,521 A | 7/1998 | Rheinheimer et al. |
| 5,948,421 A | 9/1999 | Okano et al. |
| 6,031,153 A | 2/2000 | Ryals et al. |
| 6,060,074 A | 5/2000 | Butler, Jr. et al. |
| 6,160,001 A | 12/2000 | Assmann et al. |
| 6,172,083 B1 | 1/2001 | Wagner et al. |
| 6,177,414 B1 | 1/2001 | Tomalia et al. |
| 6,177,446 B1 | 1/2001 | Wagner et al. |
| 6,194,417 B1 | 2/2001 | Müller et al. |
| 6,241,795 B1 | 6/2001 | Svec et al. |
| 6,245,770 B1 | 6/2001 | Bereznak et al. |
| 6,248,731 B1 | 6/2001 | Blahut |
| 6,318,023 B1 * | 11/2001 | Yamashita ................. 47/58.1 |
| 6,413,910 B1 * | 7/2002 | Vasiljevich et al. ......... 504/140 |

FOREIGN PATENT DOCUMENTS

| | | |
|---|---|---|
| EP | 0 878 129 | 11/1998 |
| EP | 1 036 499 | 9/2000 |
| JP | 2000-212013 | * 8/2000 |
| JP | 2001-152152 | 6/2001 |

OTHER PUBLICATIONS

Patent Abstracts of Japan, vol. 2000, No. 23, Feb. 10, 2001, Abstract.
Database WPI, Section CH., Week 200055, Derwent Publications Ltd., London, AN 2000–582008, XP002237361.
Inbar, et al., Elicitors Of Plant Defensive Systems Reduce Insect Densities And Disease Incidence, Journal of Chemical Ecology, 1998, pp. 135–149, v. 24, No. 1, Plenum Publishing Corporation.
Klessig, et al., The Salicylic Acid Signal In Plants, Plant Molecular Biology, 1994, pp. 1439–1458, v. 26, Kluwer Academic Publishers, Belgium.
McCollum, et al., Exploitation Of Plant Pathogenesis–Related Proteins For Enhanced Pest Resistance In Citrus, Proc. Fla. State Hort. Soc., 1995, pp. 88–92, v. 108.

* cited by examiner

Primary Examiner—S. Mark Clardy
(74) Attorney, Agent, or Firm—Banner & Witcoff, Ltd.

(57) ABSTRACT

The invention provides stable, aqueous formulations comprising high concentrations of salicylic acid and hydrolyzed chitosan, which can be used to prepare diluted, working formulations for enhancing plant defensive responses.

54 Claims, 1 Drawing Sheet

STABILIZED CONCENTRATED FORMULATIONS FOR ENHANCING PLANT DEFENSIVE RESPONSES

FIELD OF THE INVENTION

This invention relates to the development of a chemically stable formulation of plant defensive response elicitors and their use in agricultural and horticultural crops.

BACKGROUND OF THE INVENTION

Plants have developed a number of defensive strategies against pathogens and herbivores. These include structural modifications such as leaf shape, thorns, and trichomes, as well as varied biochemical strategies developed by plants to deter insect and pathogen attacks. The innate ability of plants to resist insect feeding and pathogen infection is known but little understood. It has, however, been used as selection criteria by classical plant breeders in developing new resistant crop varieties. In recent years, using new technologies scientists have made great strides in understanding the mechanisms of plant defenses and the molecular components involved.

Plant Defense Responses

To date, four distinct but overlapping plant defensive responses have been identified. These are the hyper sensitive response (HR), the wounding response (WR), the systemic acquired resistance response (SAR), and the induced systemic resistance response (ISR) (1,2).

The hyper sensitive response (HR) is the first line of defense used by plants against pathogen infections and occurs rapidly after the detection of the pathogen at the site of infection. The characteristic feature of this mechanism is the development of lesions, whereby the plant cells surrounding the infection site die either thorough direct interaction with the pathogen or by an endogenous self-destruct mechanism to produce lesions, hence reducing the spread of the pathogen.

Wounding or insect feeding activates the Wound Response. In this response, the plant produces a number of proteins, including proteinase inhibitors. As the insect continues to feed on plant tissues, it will start to ingest the newly synthesized proteins. The function of the plant proteinase inhibitor proteins is to inhibit the insect's digestive enzymes and hence deter its feeding.

Following the HR and or WR responses, the plant produces a number of proteins, collectively referred to as pathogenesis related (PR) proteins (3). The PR proteins are synthesized not only locally at the point of attack, but also systemically through out the plant. This second stage response is known as Systemic Acquired Resistance (SAR). The SAR response primes the whole plant to repel the pathogen or insect, not only at the original point but also throughout the plant.

The above three pathways are initiated by the plant in response to infection or insect feeding which could cause harm to the plant. The ISR response, however, is distinct because its activation is caused by non-pathogenic and beneficial rhizobacteria and the components of their cell walls. The ISR response acts to "immunize" the plant against infection by pathogenic organisms (4, 5).

The ability of a plant to develop a systemic resistance after localized infection or wounding indicates that it possesses signaling mechanisms, which not only alerts cells close to the point of infection or injury but also cells distal to the interaction site.

Signaling Molecules Involved in the Plant Defensive Response

Unlike animals, plants do not possess a nervous system. Instead, plants have developed signal molecules to facilitate communication between cells. Three prominent signaling molecules used by plants also play major roles in initiating the defense response. These molecules are salicylic acid (SA), jasmonic acid (JA), and ethylene.

Salicylic acid ($C_7H_6O_3$) is a phenolic compound produced by plants and is the key signal molecule for the initiation of the SAR response (6, 7) after pathogen infection (FIG. 1). The plant growth regulators jasmonic acid ($C_{12}H_{18}O_3$) (8) and ethylene (9) have also been shown to play key roles in the plant defensive responses (9–14). Ethylene and JA appear to work synergistically to initiate the SA independent pathways (FIG. 1) (15, 16). Even though these signals are produced in response to different stimuli and initiate different plant responses (17), they have significant effect on one another's modes of action. For example, it has been shown that induction of the SAR response by exogenous application of SA has a negative effect on the synthesis and mode of action of JA and ethylene (18, 19).

There is also sufficient evidence available to suggest the presence of other endogenous plant signaling molecules whose nature and mode of action is yet to be determined. The plant defense response, however, is not solely mediated by endogenous plant signals. Exogenous molecules, both synthetic (36) and those produced through the interaction of the invading organism with the plant, have also been shown to act as elicitors of the plant defense responses (20, 21). The biopolymer chitosan is one such molecule. Chitosan is a long chain polymer of glucosamine molecules linked together via β-(1,4) linkages and is a cell wall component of a number of fungi (22, 23). Chitosan has been shown to have some direct anti-fungal and antibacterial activities (24, 25) and has been proposed for use as a food preservative.

Application of chitosan to plants causes a number of different physiological responses. It reduces the stomatal apertures of the leaf, thus reducing the ability of pathogens to gain access into the plant (26), causes the production of phenolic compounds (27, 28), and increases crop yields (29, 30). Chitosan also acts as an effective elicitor of the plant defense response and causes a decrease in disease incidence in treated crops (31–35).

Synergistic Effect of Salicylic Acid and Chitosan

Recently, the application of plant defensive elicitors has been recognized as a viable alternative to the use of more traditional pesticides, and new commercial products such as Messenger® and Actigard® have been developed (21, 36). Because the plant defense response is mediated by a number of signaling molecules that activate different plant defensive pathways, the external application of a single elicitor would under-utilize the full array of defensive responses available to the plant. In addition, the plant defense response is transient, i.e., the genes involved are switched on due to a stimulus, such as a pathogen or insect attack. After the stimulus is removed, the plant switches off the genes. Typically within six weeks after the removal of the stimulant (elicitor), the plant gradually degrades and reabsorbs the defensive gene products. Because the plant defense response is transient in nature, in order to utilize it as a viable method of protection it is necessary to constantly stimulate the plant.

After foliar or soil application, salicylic acid is readily taken up by plants and induces the SAR response. It is however, short-lived both in the plant and in the environment (37), which limits its effectiveness as an elicitor. In addition, in some plants salicylic acid's induction of SAR causes a shut down of the JA-induced pathways (18, 19). Chitosan, on the other hand, is more stable and is gradually absorbed by the plant. It also has a broader range of activities, acting both on the salicylic acid-dependent and salicylic acid-independent pathways. It also mitigates some of the effects of salicylic acid on the other defensive pathways (18, 31). The elicitor effect of chitosan is dependent on the degree of polymerization of the molecules. Chitosan oligomers of between 2–50 monomers in length have been shown to be the most effective in eliciting the plant's defensive responses.

The combinational use of SA and chitosan has a synergistic effect whereby SA allows for a rapid induction of the SAR response, which is then maintained and augmented through the slower action of the chitosan as it is gradually absorbed by the plant. Long chain chitosan polymers as well as short chain chitosan polymers are, however, practically insoluble at pH 7 or above. Thus, there is a need in the art for a method of preparing a formulation of chitosan and salicylic acid, which allows for the solubilization of all the components over a wide range of pH values.

BRIEF SUMMARY OF THE INVENTION

It is an object of the invention to provide stable aqueous formulations of chitosan and salicylic acid. This and other objects of the invention are provided by one or more of the embodiments described below.

One embodiment of the invention is a stable aqueous formulation comprising at least about 4% salicylic acid, hydrolyzed chitosan in a molar ratio with the salicylic acid ranging from about 0.01:1 to about 3:1, an inorganic base in a molar ratio with the salicylic acid of about 0.2:1 to about 3:1, and humic acid in a weight to weight ratio with the hydrolyzed chitosan ranging from about 1:1 to about 1:10.

Another embodiment of the invention is a stable aqueous formulation comprising at least about 2% hydrolyzed chitosan, salicylic acid in a molar ratio with the hydrolyzed chitosan ranging from about 1:0.01 to about 1:3, an inorganic base in a molar ratio with the salicylic acid of about 0.2:1 to about 3:1, and humic acid in a weight to weight ratio with the hydrolyzed chitosan ranging from about 1:1 to about 1:10.

Yet another embodiment of the invention is a stable aqueous formulation comprising at least about 4% salicylic acid, at least about 2% hydrolyzed chitosan, wherein the hydrolyzed chitosan is present in a molar ratio with the salicylic acid ranging from about 0.01:1 to about 3:1, an inorganic base in a molar ratio with the salicylic acid of about 0.2:1 to about 3:1, and humic acid in a weight to weight ratio with the hydrolyzed chitosan ranging from about 1:1 to about 1:10.

Even another embodiment of the invention is a stable aqueous formulation comprising at least about 4% salicylic acid, hydrolyzed chitosan in a molar ratio with the salicylic acid of about 1:1, an inorganic base in a molar ratio with the salicylic acid of about 1:1, and humic acid in a weight to weight ratio with the hydrolyzed chitosan of about 1:7.

A further embodiment of the invention is a stable aqueous formulation comprising at least about 4% salicylic acid, hydrolyzed chitosan in a molar ratio with the salicylic acid ranging from about 0.01:1 to about 3:1, an inorganic base in an amount sufficient to stabilize the salicylic acid, and humic acid in an amount sufficient to stabilize the hydrolyzed chitosan.

Another embodiment of the invention is a stable aqueous formulation comprising at least about 2% hydrolyzed chitosan, salicylic acid in a molar ratio with the hydrolyzed chitosan ranging from about 1:0.01 to about 1:3, an inorganic base in an amount sufficient to stabilize the salicylic acid, and humic acid in an amount sufficient to stabilize the hydrolyzed chitosan.

Still another embodiment of the invention is a method of making a stable aqueous formulation of salicylic acid and chitosan. Hydrolyzed chitosan is added to a first aqueous solution to form a second aqueous solution. The first aqueous solution comprises salicylic acid and an inorganic base in an amount sufficient to stabilize the salicylic acid. Humic acid is added to the second solution in an amount sufficient to stabilize the hydrolyzed chitosan. The stable formulation comprises at least about 4% salicylic acid. The salicylic acid and the hydrolyzed chitosan are present in a molar ratio ranging from about 1:0.01 to about 1:3. The inorganic base and the salicylic acid are present in a molar ratio of about 0.2:1 to about 3:1. The humic acid and the hydrolyzed chitosan are present in a weight to weight ratio ranging from about 1:1 to about 1:10.

Yet another embodiment of the invention is a method of making a stable aqueous formulation of salicylic acid and chitosan. Hydrolyzed chitosan is added to a first aqueous solution to form a second aqueous solution. The first aqueous solution comprises salicylic acid and an inorganic base in an amount sufficient to stabilize the salicylic acid. Humic acid is added to the second solution in an amount sufficient to stabilize the hydrolyzed chitosan. The stable formulation comprises at least about 2% humic acid. The salicylic acid and the hydrolyzed chitosan are present in a molar ratio ranging from about 1:0.01 to about 1:3. The inorganic base and the salicylic acid are present in a molar ratio of about 0.2:1 to about 3:1. The humic acid and the hydrolyzed chitosan are present in a weight to weight ratio ranging from about 1:1 to about 1:10.

Another embodiment of the invention is a stable aqueous formulation made by adding hydrolyzed chitosan to a first aqueous solution to form a second aqueous solution. The first aqueous solution comprises salicylic acid and an inorganic base in an amount sufficient to stabilize the salicylic acid. Humic acid is added to the second solution in an amount sufficient to stabilize the hydrolyzed chitosan. The stable formulation comprises at least about 4% salicylic acid. The salicylic acid and the hydrolyzed chitosan are present in a molar ratio ranging from about 1:0.01 to about 1:3. The inorganic base and the salicylic acid are present in a molar ratio of about 0.2:1 to about 3:1. The humic acid and the hydrolyzed chitosan are present in a weight to weight ratio ranging from about 1:1 to about 1:10.

Yet another embodiment of the invention is a stable aqueous formulation made by adding hydrolyzed chitosan to a first aqueous solution to form a second aqueous solution. The first aqueous solution comprises salicylic acid and an inorganic base in an amount sufficient to stabilize the salicylic acid. Humic acid is added to the second solution in an amount sufficient to stabilize the hydrolyzed chitosan. The stable formulation comprises at least about 2% humic acid. The salicylic acid and the hydrolyzed chitosan are present in a molar ratio ranging from about 1:0.01 to about 1:3. The inorganic base and the salicylic acid are present in a molar ratio of about 0.2:1 to about 3:1. The humic acid and the hydrolyzed chitosan are present in a weight to weight ratio ranging from about 1:1 to about 1:10.

Still another embodiment of the invention is a stable aqueous formulation comprising about 31% salicylic acid, about 16% hydrolyzed chitosan, about 11% potassium hydroxide, and about 2% humic acid.

A further embodiment of the invention is a method of making a stable aqueous formulation of salicylic acid and hydrolyzed chitosan. Hydrolyzed chitosan is added to a first aqueous solution to form a second aqueous solution. The first aqueous solution comprises salicylic acid and an inorganic base in an amount sufficient to stabilize the salicylic acid. Humic acid is added to the second solution in an amount sufficient to stabilize the hydrolyzed chitosan. The stable formulation comprises at least about 31% salicylic acid and at least about 16% chitosan.

Another embodiment of the invention is a stable aqueous formulation made by adding hydrolyzed chitosan to a first aqueous solution to form a second aqueous solution. The first aqueous solution comprises salicylic acid and an inorganic base in an amount sufficient to stabilize the salicylic acid. Humic acid is added to the second solution in an amount sufficient to stabilize the hydrolyzed chitosan. The stable formulation comprises at least about 31% salicylic acid and at least about 16% chitosan.

Yet another embodiment of the invention is a method of enhancing a plant defensive response against a pathogen or herbivore. A plant is contacted with a formulation comprising about 5% by weight of a stable formulation made by adding hydrolyzed chitosan to a first aqueous solution to form a second aqueous solution. The first aqueous solution comprises salicylic acid and an inorganic base in an amount sufficient to stabilize the salicylic acid. Humic acid is added to the second solution in an amount sufficient to stabilize the hydrolyzed chitosan. The stable formulation comprises at least about 4% salicylic acid. The salicylic acid and the hydrolyzed chitosan are present in a molar ratio ranging from about 1:0.01 to about 1:3. The inorganic base and the salicylic acid are present in a molar ratio of about 0.2:1 to about 3:1. The humic acid and the hydrolyzed chitosan are present in a weight to weight ratio ranging from about 1:1 to about 1:10. The plant's defensive response is thereby enhanced.

Yet another embodiment of the invention is a method of enhancing a plant defensive response against a pathogen or herbivore. A plant is contacted with a formulation comprising about 5% by weight of a stable formulation made by adding hydrolyzed chitosan to a first aqueous solution to form a second aqueous solution. The first aqueous solution comprises salicylic acid and an inorganic base in an amount sufficient to stabilize the salicylic acid. Humic acid is added to the second solution in an amount sufficient to stabilize the hydrolyzed chitosan. The stable formulation comprises at least about 2% humic acid. The salicylic acid and the hydrolyzed chitosan are present in a molar ratio ranging from about 1:0.01 to about 1:3. The inorganic base and the salicylic acid are present in a molar ratio of about 0.2:1 to about 3:1. The humic acid and the hydrolyzed chitosan are present in a weight to weight ratio ranging from about 1:1 to about 1:10. The plant's defensive response is thereby enhanced.

The invention thus provides stable, aqueous formulations comprising chitosan and salicylic acid, as well as methods of making such formulations and using them to enhance plant defensive responses.

DETAILED DESCRIPTION OF THE INVENTION

Figure 1:
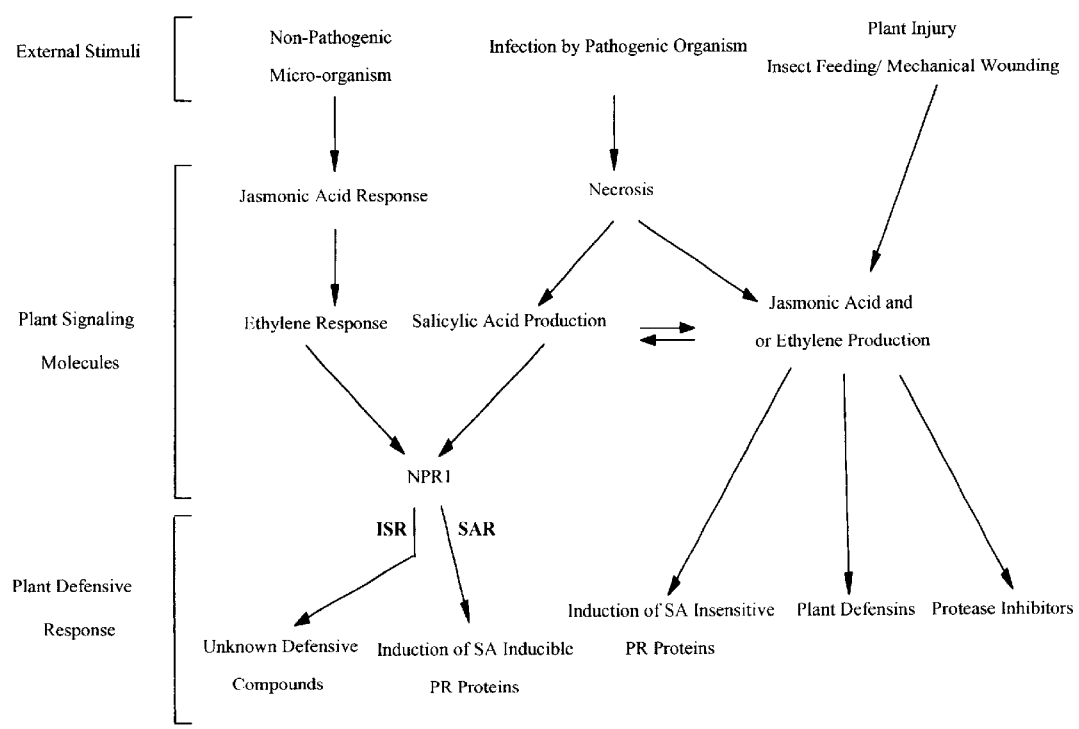
FIG. 1. Diagram of plant defensive responses.

Even though the ability of both salicylic acid and chitosan to act as elicitors of plants defensive responses have been well established, due to their chemical properties the use of these compounds in concert in a liquid formulation has proven difficult. In solution, salicylic acid and its derivatives have been shown to be unstable and undergo rapid degradation and polymerization. Blahut, U.S. Pat. No. 6,248,731, teaches that that salicylic acid can be stabilized in solution at or near neutral pH if it is reacted with potassium hydroxide. Both long and short chain chitosan polymers, however, are practically in soluble at pH 7 or above.

It is a discovery of the present invention that the addition of hydrolyzed chitosan and humic acid to a solution of a strong base and salicylic acid permits all components to be solubilized over a wide range of pH values. The present invention thus discloses a stable, concentrated aqueous formulation of salicylic acid and hydrolyzed chitosan and a method for its preparation. The concentrated formulation can be diluted and used to enhance a plant's defensive responses in agricultural and horticultural crops.

The advantage of this formulation is not only its capacity to maintain the different components in solution, but also its ability to stabilize the solutes in their original chemical profiles. This chemical stability allows the efficacious use of these compounds as elicitors of plant defensive responses. Moreover, the concentrated formulation is less expensive to store and can be diluted to a working formula as needed.

In addition, components such as plant micronutrients, macronutrients, nitrogen, phosphate, and potash, can be added to the concentrated formulation to form a wide variety of working formulations useful for eliciting plant defensive responses and enhancing the growth and health of plants.

A variety of crops can be treated with the working formulations, including cotton, trees, grasses, coffee, cereals (e.g., wheat, sorghum, barley, oats, rye, maize, rice), beets (e.g., sugar beet and fodder beat), pomes, stone fruit and soft fruit (e.g., apples, pears, plums, peaches, almonds, cherries, strawberries, raspberries, and blackberries), leguminous plants (e.g., beans, lentils, peas, soybeans), oil plants (e.g., rape, mustard, poppy, olives, sunflowers, coconut, castor oil plants, cocoa beans, groundnuts), cucumber plants (e.g., marrows, cucumber, melons), fiber plants (e.g., cotton, flax, hemp, jute), citrus fruit (e.g., oranges, lemons, grapefruit, mandarins), vegetables (e.g., spinach, lettuce, asparagus, cabbages, carrots, onions, tomatoes, potatoes, paprika), lauraceae (avocados, cinnamon, camphor), plants such as tobacco, nuts, coffee, sugar cane, tea, vines, hops, bananas, and natural rubber plants, and ornamentals (e.g., flowers, shrubs, broad-leaved trees, and evergreens).

Formulation

Stable, concentrated aqueous formulations of the invention comprise four basic components: salicylic acid, an inorganic base, hydrolyzed chitosan, and humic acid. Such formulations are referred to in the Examples as "SSAX." The concentration of either salicylic acid and/or hydrolyzed chitosan in stable formulations of the invention, however, is greater than that in prior formulations. In formulations of the invention, the concentration of salicylic acid is at least about 4% and/or the concentration of hydrolyzed chitosan is at least about 2%. Salicylic acid concentrations range from at least about 4% to about 8, 12, 15, 25, or 30%. Hydrolyzed chitosan concentrations range from at least about 2% to about 5, 10, or 15%. The molar ratios of salicylic acid and hydrolyzed chitosan range from about 1:0.01 to about 1:3. For example, salicylic acid and hydrolyzed chitosan can be present in stable formulations of the invention in a molar ratio of about 1:0.01, 1:0.1, 1:1, 1:2, or 1:3. A preferred molar ratio is about 1:1.

Salicylic acid for use in formulations of the invention can be purchased from commercial suppliers or can be prepared using methods long-known in the art. See, e.g., U.S. Pat. No. 4,131,618. Formulations of the invention are stable over a wide range of pH values (e.g., pH of about 2 to pH of about 8) and for long periods of time. Preferred formulations show no visible sign of precipitation at ambient temperature (e.g., about 15 to about 35° C.) for at least 6 months. Moreover, the individual components remain chemically distinct; in fact, 95% of the dissolved salicylic acid and its salt can be recovered from the solution using four parts ethanol after two weeks. The chitosan molecules are hydrogen bonded to the humic acid and remain stable and in solution indefinitely.

Chitosan can be purchased commercially or can be prepared, for example, as taught in U.S. Pat. No. 5,232,842. Preferably, the chitosan in the formulation of the invention is a mixture of various size chitosan molecules each comprising from about two to about 10, 20, 25, 50, 75, 100, 150, 200, 250, 300, 350, 400, 450, or 500 glucosamine molecules. Long chain chitosan molecules can be hydrolyzed by either enzymatic or chemical methods to produce short chain molecules of the desired size. Preferably, no more than 20% of the amine groups of each chitosan molecule are acetylated. Acetylation of chitosan is taught in U.S. Pat. No. 4,996,307.

Any strong inorganic base can be used in the formulation of the invention. Suitable inorganic bases are, for example, potassium hydroxide, ammonium hydroxide, sodium hydroxide, and mixtures of these bases. Potassium hydroxide is preferred. The inorganic base is present in an amount sufficient to stabilize the salicylic acid. The molar ratio of the inorganic base to the salicylic acid preferably ranges from about 0.2:1 to about 3:1. Molar ratios of about 0.2:1, 0.3:1, 0.4:1, 0.5:1, 0.75:1, 1:1, 1.25:1, 1.5:1, 1.75:1, 2:1, 2.5:1, or 3:1 are acceptable. A molar ratio of 1:1 is preferred.

Humic acid can be purchased commercially or can be prepared, for example, as taught in U.S. Pat. No. 3,111,404, 3,544,296, 3,770,411, 3,398,186, 3,076,291, 3,222,160, or 4,319,041. Humic acid is present in stable formulations of the invention in an amount sufficient to stabilize the hydrolyzed chitosan. Preferably, the humic acid is present in a weight to weight ratio with the hydrolyzed chitosan of about 1:1 to about 1:10. Ranges of about 1:1, 1:2, 1:3, 1:4, 1:5, 1:6, 1:7, 1:8, 1:9, or 1:10 are acceptable. A weight to weight ratio of about 1:7 is preferred.

Preferred product formulations are shown in Tables 1 and 2, below.

TABLE 1

| Components | % Total (w/w) |
| --- | --- |
| Water | 16.32 |
| 45% (w/v) solution of KOH | 25.51 |
| Salicylic acid | 30.61 |
| Hydrolyzed chitosan | 16.34 |
| 20% (w/v) solution of humic acid | 11.22 |
| Total | 100.00 |

TABLE 2

| Components | Ratios |
| --- | --- |
| KOH: salicylic acid | 1:1 (molar) |
| KOH: hydrolyzed chitosan | 1:0.5 (molar) |
| hydrolyzed chitosan: salicylic acid | 1:1 (molar) |
| hydrolyzed chitosan: humic acid | 7:1 (weight) |

Stable concentrated formulations of the invention can comprise additional components, such as plant micronutrients. The additional components can be added to the aqueous formulation of the invention, either in its concentrated or in a diluted, working form. Compounds comprising, for example, magnesium, manganese, iron, boron, molybdenum, zinc, potassium, sodium, or calcium can be added. These components can be used as salts (e.g., sulfate or molybdate salts) or chelated with compounds such as EDTA, glucoheptonate, or humic acid. Other components, such as yeast hydrolysate and Solubor®, plant micronutrients, nitrogen, phosphate, fungicides, or potash, also can be added.

Method of Making a Stable Aqueous Formulation of Neutralized Salicylic Acid and Hydrolyzed Chitosan The stable aqueous formulation of the invention is made by first preparing an aqueous solution of salicylic acid and an inorganic base, preferably potassium hydroxide. This can be done, for example, as described in U.S. Pat. No. 6,248,731. The inorganic base preferably is present in an amount sufficient to stabilize the salicylic acid, i.e., to permit the salicylic acid to remain solubilized in the same solution as the hydrolyzed chitosan and to maintain its chemical characteristics.

A preferred method for preparing stable aqueous formulations of the invention is to add hydrolyzed chitosan to an aqueous solution comprising salicylic acid and an inorganic base, then to add humic acid to the salicylic acid-base solution. Humic acid is preferably present in an amount sufficient to stabilize the hydrolyzed chitosan, i.e., to permit the hydrolyzed chitosan to remain solubilized in the same solution as the salicylic acid and to maintain its chemical characteristics. Use of a 20% solution of humic acid is preferred.

The resultant mixture is stirred until all the components are dissolved (approximately 1 hour). If foaming occurs after or during the mixing, mixing should be discontinued to allow the foam to dissipate. Addition of anti-foaming agents is not desired.

Working formulations of the invention can be used in any type of topical application, including both foliar and soil applications. To prepare working formulations for use in eliciting plant defensive responses, stable aqueous formulations of the invention can be diluted from about 0.2% to about 20% (weight/weight), depending on the type and size of the crop to be treated. Dilutions of from about 0.2% to about 2%, about 0.5% to about 5%, about 2% to about 10%, about 5% to about 15%, and about 15% to about 20% can be used. If desired, solutions of plant micronutrients or other additives, as described above, can be used to dilute the concentrated formulation. See Example 2.

All patents and patent applications cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Method of Preparing a Stable Aqueous Formulation of Salicylic Acid and Hydrolyzed Chitosan Water not containing dissolved iron (16.32 pounds) was decanted into a stainless steel tank. Potassium hydroxide (25.51 pounds of a 45% weight per volume solution) was added to the reaction vessel and mixed thoroughly to produce a homogenous mixture.

Gradually, 30.61 pounds of salicylic acid was added to the alkaline solution and mixed continuously until all of the salicylic acid was dissolved. While continuously stirring, 16.34 pounds of hydrolyzed chitosan was slowly incorporated into the mixture. Before addition, the hydrolyzed chitosan was dissolved in a dilute solution of HCl to a pH of about 2.

Finally, 11.2 pounds of a 20% weight per volume aqueous solution of humic acid was added to the mixture. The mixture was stirred until all the ingredients were dissolved.

EXAMPLE 2

Independent Growth Comparison

Speedling type planting trays (11×22 cells) were sterilized, rinsed, filled with Pro-Mix 'VFT,' and moistened with sufficient water for seeding with tomato variety 'Florida 47' (Asgrow Seed Company). Treatment and control plants were replicated 4 times and blocked down the row giving a randomized complete block design. The remaining flats were wet with plain water. The seedlings were grown in a commercial type greenhouse and watered daily using an automated traveling boom. Fertilizer, 20–20–20 N—P—K, at approximately 50 ppm N was delivered through the irrigation system at watering 2 to 3 times per week. Appropriate fungicides and a *Bacillus thurigiensis* were applied to control diseases and insects. A solution containing 5% (w/w) SSAX, 1.5% (w/w) chelated magnesium, 0.16% (w/w) chelated boron, 3.5% (w/w) chelated iron, 0.75% (w/w) chelated manganese, 0.003% (w/w) chelated molybdenum and 0.75% chelated zinc was applied to the foliage of tomato seedlings 3 weeks and 5 weeks after planting. At five weeks, the seedlings were sampled for growth comparisons. Seedlings were transplanted to the field in order to compare growth and yield. Plants were treated with a root drench at transplantation, and with foliar applications once a week.

The results are shown in Tables 3–5.

TABLE 3

Seedling Parameters After 5 Weeks Growth in the Green House.

| Treatment | Stem length (cm) | Stem Dia. (cm) | Leaf Area (cm2) | Dry Shoot (g) | Dry Root (g) | True Leaf (No.) | Root Shoot Ratio |
|---|---|---|---|---|---|---|---|
| Test | 11.0 | 2.44 | 14.26 | 0.1363 | 0.0366 | 2.8 | 0.2743 |
| Control | 10.9 | 2.35 | 13.71 | 0.1304 | 0.0328 | 2.6 | 0.2529 |

TABLE 4

Field Sample Data.

| | 30 DAT | 60 DAT | | |
|---|---|---|---|---|
| Treatment | Dry Shoot (g) | Dry Shoot (g) | Fresh Fruit (no) | Fruit Wt (g) |
| Test | 10.29 | 148.2 | 31.7 | 576 |
| Control | 8.66 | 146.2 | 22.7 | 328 |

TABLE 5

Yield Data After Field Transplantation.

| | Reds and Breakers | | | | | Mature Green | | | | | | |
|---|---|---|---|---|---|---|---|---|---|---|---|---|
| Treatment | Sm. | Med | Lg. | X-Lg | Total | Sm. | Med. | Lg. | X-Lg | Total | Red & Green | Cull |
| FIRST HARVEST | | | | | | | | | | | | |
| Test | — | 1.3 | 2.4 | 21.3 | 25.0 | — | 0.4 | 3.1 | 18.4 | 21.9 | 46.9 | 3.8 |
| Control | — | 0.9 | 2.2 | 12.0 | 15.2 | — | 0.9 | 5.9 | 20.7 | 27.5 | 42.7 | 1.9 |
| SECOND HARVEST | | | | | | | | | | | | |
| Test | 0.4 | 1.0 | 0.7 | 1.5 | 3.6 | 14.8 | 19.1 | 9.5 | 6.9 | 50.3 | 53.9 | 0.9 |
| Control | 0.6 | 0.9 | 0.0 | 0.8 | 2.3 | 15.1 | 17.9 | 7.4 | 5.5 | 45.9 | 48.2 | 0.1 |
| TOTAL | | | | | | | | | | | | |
| Test | 0.4 | 2.3 | 3.2 | 22.8 | 28.6 | 14.8 | 19.5 | 12.6 | 25.3 | 72.2 | 100.8 | 4.7 |
| Control | 0.6 | 1.8 | 2.2 | 12.8 | 17.4 | 15.1 | 18.8 | 13.4 | 26.2 | 73.4 | 90.9 | 2.0 |

EXAMPLE 3

Effect of Treatment on Bacterial Leaf Spot Infection of Tomato Leaves.

Tomato plants were transplanted at 6-weeks age to 6" pots and placed in the greenhouse for one week. Plants were inoculated 7 days after transplanting with a suspension of *Xanthomonas campestris* pv. *vesicatoria*. The inoculum contained tomato race 1 and 3 of *X. cv.* mixed equally at $10^4$ colony-forming units per ml and was sprayed onto plants until runoff, with a handheld aerosol canister. The number of bacterial spots per plant was counted at 7-day intervals for 4 weeks. The numbers from four replications of each treatment were subjected to ANOVA and the means tested by Duncans Multiple Range Test.

The results are shown in Tables 6 and 7.

TABLE 6

| | Trial 1 | | | | |
|---|---|---|---|---|---|
| Treatments | Sept. 21 | Sept. 28 | Oct. 5 | Oct. 12 | AUDPC* |
| Test | 1.35 b | 2.75 d | 7.6 a | 9.85 ab | 111.65 b |
| Control | 2.3 b | 5.2 ab | 8.8 a | 7.7 ab | 133.00 ab |

*AUDPC = Area Under the Disease Progress Curve (9/21–10/12)

TABLE 7

| | Trial 2 | | | |
|---|---|---|---|---|
| Treatments | Nov. 2 | Nov. 8 | Nov. 17 | AUDPC* |
| Test | 12.615 ab | 4.026 b | .343 abc | 69.580 b |
| Control | 16.087 a | 6.858 a | .553 a | 102.186 a |

AUDPC = Area Under the Disease Progress Curve

EXAMPLE 4

Effect of Treatment on Nematode Infestation of Tomato Roots.

Experiments were maintained in the greenhouse, fertilized once a week, weeded by hand, and treated with insecticide as necessary. All studies were transplanted into 4" pots with thoroughly mixed Sanford, Fla., field soil that was naturally infested with *Meloidogyne incognita* (root-knot nematode). Tomato seedlings were set up in randomized complete blocks with 15 replications and were evaluated after four weeks.

Pre-Plant Analysis—At the time of transplanting into field soil, five transplants were destructively sampled for root analysis using the WinRhizo software package.

Post-Plant Analysis—Once a week, trials were evaluated for disease and chlorosis. After four weeks, plants were washed and analyzed for the following:

1. Terminal Shoot Length—Measurement in centimeters taken from the last mature leaf to the tip of the root system.
2. Fresh Shoot Weight—Root system measurement in grams.
3. Basal Diameter—Shoot measurement in grams.
4. Overall Root Condition—Scale of 1–5; 1=good, 5=bad.
5. Nematode Gall Rate—Rate taken on nematode galling in by Zeck's index; 0=no galling, 10=complete galling.
6. Dry Root Weight—Root system measurement in grams.
7. Dry Shoot Weight—Shoot measurement in grams.

The results are shown in Tables 8–11.

TABLE 8

Pre-Plant Root Analysis (Trial 1)

| Treatment | Projected Area | Surface Area | Average Dia. | Root Volume | Tips | Forks | Crossings |
|---|---|---|---|---|---|---|---|
| Test | 44.094 | 138.53 | 10.30 | 35.06 | 27.40 | 299.20 | 60.20 |
| Control | 42.965 | 134.98 | 15.33 | 51.66 | 19.40 | 301.60 | 46.00 |

TABLE 9

Post-Plant Root Analysis (Trial 1)

| Treatment | Fresh Root Wt | Fresh top Wt | Stem dia. | Length | Root Condition | Gall Rate | Dry Top Wt. | Dry Root Wt. |
|---|---|---|---|---|---|---|---|---|
| Test | 5.079** | 12.2** | 3.80** | 29.0** | 1.9692** | 5.439** | 1.206** | 0.498** |
| Control | 1.9700 | 4.646 | 3.0 | 21.636 | 3.9636 | 3.4909 | 0.5555 | 0.210 |

TABLE 10

Pre-Plant Root Analysis (Trial 2)

| Treatment | Projected Area | Surface Area | Av. Dia. | Root Vol. | Tips | Forks | Crossings |
|---|---|---|---|---|---|---|---|
| Test | 42.043** | 132.1** | 10.818* | 38.71 | 50.0** | 259.2** | 37.60** |
| Control | 30.004 | 94.26 | 13.359 | 38.94 | 11.6 | 94.80 | 7.40 |

TABLE 11

Post-Plant Root Analysis (Trial 2)

| Treatment | Root Condition | Gall Rate |
|---|---|---|
| Test | 1.3071 | 2.936 |
| Control | 1.5357 | 2.871 |

REFERENCES

1. Maleck, K. and Dietrich, A. 1999. Defense on multiple fronts: how do plants cope with diverse enemies? Trends in Plant Science 4: 215–219.
2. Pieterse, C. M. J. and Van Loon, L. C. 1999. Sailicylic acid independent plant defense pathways. Trends in Plant Science 4: 52–58.
3. Kombrink, E. and Somssich, I. E. (1997). Pathogenesis related proteins and plant defenses. In: G. C. Carrol & P. Tudzynski (eds). The Mycota V Part A, Plant Relationships. Springer-Verlag. Berlin pp. 107–128.
4. Pieterse, C. M. J. et al. (1996). Systemic resistance in Arabidopsis induced by biocontrol bacteria is independent of salicylic acid accumulation and pathogenesis-related gene expression. Plant Cell 8: 1225–1237.
5. Van Wees, S. C. M. et al. (1997). Differential induction of systemic resistance in Arabidopsis by biocontrol bacteria. Mol. Plant-Microbe Interact. 10: 716–724.
6. Gaffney, T. et al. (1993). Requirement of salicylic acid for the induction of systemic acquired resistance, Science 261: 754–756.
7. Durner, J., Shah, J. and Klessig, D. F. (1997) Salicylic acid and disease resistance in plants, Trends Plant Sci. 2: 266–274.
8. Creelman, R. A. and Mullet, J. E. (1997). Biosynthesis and action of jasmonates in plants. Annu. Rev. Plant Physiol. Plant Mol. Biol. 48: 355–381.
9. Kieber, J. J. (1997). The ethylene response pathway in Arabidopsis. Annu. Rev. Plant. Physiol. Plant Mol. Biol. 48: 277–296.
10. Vijayan, P. et al. (1998). A role for jasmonate in pathogen defense of Arabidopsis. Proc. Natl. Acad. Sci. U.S.A. 95: 7209–7214.
11. Wasternack, C. and Parthier, B. (1997). Jasmonate-signalled plant gene expression. Trends Plant Sci. 2: 302–307.
12. McConn, M. et al. (1997). Jasmonate is essential for insect defense in Arabidopsis, Proc. Natl. Acad. Sci. U.S.A. 94: 5473–5477.
13. O'Donnell, P. J. et al. (1996). Ethylene as a signal mediating the wound response of tomato plants, Science 274: 1914–1917.
14. Boller, T. (1991). Ethylene in pathogenesis and disease resistance. In: Mattoo, A. K. and Suttle, J. C., (eds). The Plant Hormone Ethylene. CRC Press. pp. 293–314.
15. Xu, Y. et al. (1994). Plant defense genes are synergistically induced by ethylene and methyl jasmonate, Plant Cell 6: 1077–1085.
16. Penninckx, I. A. M. A. et al. (1998). Concomitant activation of jasmonate and ethylene response pathways is required for induction of a plant defensin gene in Arabidopsis. Plant Cell 10: 2103–2114.
17. Thomma, B. P. H. J. et al. (1998) Separate jasmonate-dependent and salicylate-dependent defense-response pathways in Arabidopsis are essential for resistance to distinct microbial pathogens, Proc. Natl. Acad. Sci. U.S.A. 95: 15107–15111.

18. Doares, S. H. et al (1995) Salicylic acid inhibits synthesis of proteinase inhibitors in tomato leaves induced by systemin and jasmonic acid, Plant Physiol. 108: 1741–1746.
19. Niki, T. et al. (1998) Antagonistic effect of salicylic acid and jasmonic acid on the expression of pathogenesis-related (PR) protein genes in wounded mature tobacco leaves, Plant Cell Physiol. 39: 500–507.
20. Vidal, S. et al. (1998) Cell wall-degrading enzymes from *Erwinia carotovora* cooperate in the salicylic acid-independent induction of a plant defense response, Mol. Plant-Microbe Interact. 11: 23–32.
21. Wei, Z. M., et al. (1992) Harpin, elicitor of the hypersensitive response produced by the plant pathogen *Erwinia amylovora*. Science 257: 85–88.
22. Rane, K. D., (1993) Production of chitosan by fungi. Food biotechnology 7 (1): 11–33.
23. Briza, P., et al. (1999) Chemical composition of the yeast ascospore wall—the second outer layer consists of chitosan. The Journal of Biological Chemistry 263 (23): 11569–11574.
24. Rhoades, J. et al. (2000) Antimicrobial actions of degraded and native chitosan against spoilage organisms in laboratory media and foods. Applied and Environmental Microbiology 66 (1): 80–86.
25. Roller, S. et al. (1999) The antifungal properties of chitosan in laboratory media and apple juice. International Journal of Food Microbiology 47 (1/2): 67–77.
26. Lee, S., et al. (1999) Oligogalacturonic acid and chitosan reduce stomatal aperture by inducing the evolution of reactive oxygen species from guard cells of tomato and *Commelina communis*. Plant Physiology 121 (1): 147–152.
27. Bhaskara Reddy, M. V., et al. (1999) Chitosan treatment of wheat seeds induces resistance to *Fusarium graminearum* and improves seed quality. Journal of Agricultural and Food Chemistry 47 (3): 1208–1216.
28. Pitta-Alvarez, S. I., et al. (1999) Influence of chitosan, acetic acid and citric acid on growth and tropane alkaloid production in transformed roots of *Brugmansia candida*. Effect of medium pH and growth phase. Plant cell, tissue and organ culture 59: 31–38.
29. Dunand, R. T., (1995) Chitosan and yield enhancement in drill-seeded rice. Annual research report/Louisiana State University (Baton Rouge, La.). Rice Research Station. 87: 296–299.
30. Dunand, R. T., (1995) Chitosan and yield enhancement in row planted soybeans. Annual research report/ Louisiana State University (Baton Rouge, La.). Rice Research Station. 1995. 87: 409–412.
31. Doares, S. H., et al. (1995) Oligogalacturonides and chitosan activate plant defensive genes through the octadecanoid pathway. Proc. Natl. Acad. Sci. U.S.A. 92 (10): 4095–4098.
32. Benhamou, N., et al. (1998) Induction of resistance against Fusarium wilt of tomato by combination of chitosan with an endophytic bacterial strain: ultrastructure and cytochemistry of the host response. Planta 204 (2): 153–168.
33. Walker-Simmons, M. (1984) Proteinase inhibitor synthesis in tomato leaves. Induction by chitosan oligomers and chemically modified chitosan and chitin. Plant physiology 76 (3): 787–790.
34. Sathiyabama, M., et al. (1998) Chitosan induces resistance components in *Arachis hypogaea* against leaf rust caused by *Puccinia arachidis* Speg. Crop protection 17 (4): 307–313.
35. El Ghaouth, A., et al. (1994) Effect of chitosan on cucumber plants: suppression of *Pythium aphanidermatum* and induction of defense reactions. Phytopathology 84 (3): 313–320.
36. Gorlach, J., et al. (1996) Benzothiadiazole, a novel class of inducers of systemic acquired resistance, activates gene expression and disease resistance in wheat. The Plant Cell 8 (4): 629–643.
37. Klessig, D. F., Malamy, J. (1994) The salicylic acid signal in plants. Plant Molecular Biology 26: 1439–1458.

What is claimed is:

1. A method of making a stable formulation of salicylic acid and chitosan, comprising the steps of:
   adding hydrolyzed chitosan to a first aqueous solution to form a second aqueous solution, wherein the first aqueous solution comprises salicylic acid and an inorganic base in an amount sufficient to stabilize the salicylic acid; and
   adding humic acid to the second solution in an amount sufficient to stabilize the hydrolyzed chitosan, whereby a stable formulation is formed which comprises at least about 4% salicylic acid and wherein:
   the salicylic acid and the hydrolyzed chitosan are present in a molar ratio of about 2:1;
   the inorganic base and the salicylic acid are present in a molar ratio of about 1:1; and
   the humic acid is present in an amount sufficient to stabilize the hydrolyzed chitosan.

2. The method of claim 1 wherein the formulation shows no visible precipitate at ambient temperature for at least six months.

3. The method of claim 1 wherein the formulation shows no visible precipitate over a pH range of 2 to 8.

4. The method of claim 1 wherein the inorganic base is selected from the group consisting of potassium hydroxide, ammonium hydroxide, sodium hydroxide, and mixtures thereof.

5. The method of claim 1 wherein the inorganic base is potassium hydroxide.

6. The method of claim 1 wherein no more than 20% of the amine groups of the hydrolyzed chitosan molecules are acetylated.

7. The method of claim 1 further comprising the step of adding a micronutrient to the stable formulation.

8. The method of claim 7 wherein the plant micronutrient is selected from the group consisting of a boron compound, an iron compound, a magnesium compound, a manganese compound, a molybdenum compound, and a zinc compound.

9. A method of making a stable formulation of salicylic acid and chitosan, comprising the steps of:
   adding hydrolyzed chitosan to a first aqueous solution to form a second aqueous solution, wherein the first aqueous solution comprises salicylic acid and an inorganic base in an amount sufficient to stabilize the salicylic acid; and
   adding humic acid to the second solution in an amount sufficient to stabilize the hydrolyzed chitosan, whereby a stable formulation is formed which comprises at least about 2% hydrolyzed chitosan and wherein:
   the salicylic acid and the hydrolyzed chitosan are present in a molar ratio of about 2:1;and
   the inorganic base and the salicylic acid are present in a molar ratio of about 1:1.

10. The method of claim 9 wherein the formulation shows no visible precipitate at ambient temperature for at least six months.

11. The method of claim 9 wherein the formulation shows no visible precipitate over a pH range of 2 to 8.

12. The method of claim 9 wherein the inorganic base is selected from the group consisting of potassium hydroxide, ammonium hydroxide, sodium hydroxide, and mixtures thereof.

13. The method of claim 9 wherein the inorganic base is potassium hydroxide.

14. The method of claim 9 wherein no more than 20% of the amine groups of the hydrolyzed chitosan molecules are acetylated.

15. The method of claim 9 further comprising the step of adding a micronutrient to the stable formulation.

16. The method of claim 15 wherein the plant micronutrient is selected from the group consisting of a boron compound, an iron compound, a magnesium compound, a manganese compound, a molybdenum compound, and a zinc compound.

17. A method of making a stable aqueous formulation of salicylic acid and chitosan, comprising the steps of:
    adding hydrolyzed chitosan to a first aqueous solution to form a second aqueous solution, wherein the first aqueous solution comprises salicylic acid and potassium hydroxide in an amount sufficient to stabilize the salicylic acid; and
    adding humic acid to the second solution in an amount sufficient to stabilize the hydrolyzed chitosan, whereby a stable formulation is formed which comprises about 31% salicylic acid and about 16% hydrolyzed chitosan.

18. A method of enhancing a plant defensive response against a pathogen or herbivore, comprising the step of:
    contacting a plant with a formulation comprising about 5% by weight of a stable formulation made by the method of claim 1, whereby a plant defensive response is enhanced.

19. The method of claim 18 wherein the formulation further comprises a plant micronutrient.

20. The method of claim 19 wherein the plant micronutrient is selected from the group consisting of a boron compound, an iron compound, a magnesium compound, a manganese compound, a molybdenum compound, and a zinc compound.

21. A method of enhancing a plant defensive response against a pathogen or herbivore, comprising the step of:
    contacting a plant with a formulation comprising about 5% by weight of a stable formulation made by the method of claim 9, whereby a plant defensive response is enhanced.

22. The method of claim 21 wherein the formulation further comprises a plant micronutrient.

23. The method of claim 22 wherein the plant micronutrient is selected from the group consisting of a boron compound, an iron compound, a magnesium compound, a manganese compound, a molybdenum compound, and a zinc compound.

24. A stable formulation made by the method of claim 1.

25. A stable formulation made by the method of claim 9.

26. A stable aqueous formulation made by the method claim 17.

27. A stable aqueous formulation, comprising:
    at least about 4% salicylic acid;
    hydrolyzed chitosan in a molar ratio with the salicylic acid of about 1:2;
    an inorganic base in a molar ratio with the salicylic acid of about 1:1; and
    humic acid in an amount sufficient to stabilize the hydrolyzed chitosan.

28. The formulation of claim 27 wherein the formulation shows no visible precipitate at ambient temperature for at least six months.

29. The formulation of claim 27 wherein the formulation shows no visible precipitate over a pH range of 2 to 8.

30. The formulation of claim 27 wherein the inorganic base is selected from the group consisting of potassium hydroxide, ammonium hydroxide, sodium hydroxide, and mixtures thereof.

31. The formulation of claim 27 wherein the inorganic base is potassium hydroxide.

32. The formulation of claim 27 wherein no more than 20% of the amine groups of the hydrolyzed chitosan molecules are acetylated.

33. The formulation of claim 27 further comprising a plant micronutrient.

34. The formulation of claim 33 wherein the plant micronutrient is selected from the group consisting of a boron compound, an iron compound, a magnesium compound, a manganese compound, a molybdenum compound, and a zinc compound.

35. A stable aqueous formulation, comprising:
    at least about 2% hydrolyzed chitosan;
    salicylic acid in a molar ratio with the hydrolyzed chitosan of about 2:1;
    an inorganic base in a molar ratio with the salicylic acid of about 1:1; and
    humic acid in an amount sufficient to stabilize the hydrolyzed chitosan.

36. The formulation of claim 35 wherein the formulation shows no visible precipitate at ambient temperature for at least six months.

37. The formulation of claim 35 wherein the formulation shows no visible precipitate over a pH range of 2 to 8.

38. The formulation of claim 35 wherein the inorganic base is selected from the group consisting of potassium hydroxide, ammonium hydroxide, sodium hydroxide, and mixtures thereof.

39. The formulation of claim 35 wherein the inorganic base is potassium hydroxide.

40. The formulation of claim 35 wherein no more than 20% of the amine groups of the hydrolyzed chitosan molecules are acetylated.

41. The formulation of claim 35 further comprising a plant micronutrient.

42. The formulation of claim 41 wherein the plant micronutrient is selected from the group consisting of a boron compound, an iron compound, a magnesium compound, a manganese compound, a molybdenum compound, and a zinc compound.

43. A stable aqueous formulation, comprising:
    at least about 4% salicylic acid;
    at least about 2% hydrolyzed chitosan, wherein the hydrolyzed chitosan is present in a molar ratio of about 1:2 with the salicylic;
    an inorganic base in a molar ratio with the salicylic acid of about 1:1; and
    humic acid in an amount sufficient to stabilize the hydrolyzed chitosan.

44. A stable aqueous formulation, comprising:
    at least about 4% salicylic acid;
    hydrolyzed chitosan in a molar ratio with the salicylic acid of about 1:2;
    an inorganic base in an amount sufficient to stabilize the salicylic acid; and
    humic acid in an amount sufficient to stabilize the hydrolyzed chitosan.

45. The formulation of claim 44 wherein the inorganic base is potassium hydroxide.

46. The formulation of claim 44 wherein no more than 20% of the amine groups of the hydrolyzed chitosan molecules are acetylated.

47. The formulation of claim 44 further comprising a plant micronutrient.

48. The formulation of claim 47 wherein the plant micronutrient is selected from the group consisting of a boron compound, an iron compound, a magnesium compound, a manganese compound, a molybdenum compound, and a zinc compound.

49. A stable aqueous formulation, comprising:
- at least about 2% hydrolyzed chitosan;
- salicylic acid in a molar ratio with the hydrolyzed chitosan of about 2:1;
- an inorganic base in an amount sufficient to stabilize the salicylic acid; and
- humic acid in an amount sufficient to stabilize the hydrolyzed chitosan.

50. The formulation of claim 49 wherein the inorganic base is potassium hydroxide.

51. The formulation of claim 49 wherein no more than 20% of the amine groups of the hydrolyzed chitosan molecules are acetylated.

52. The formulation of claim 49 further comprising a plant micronutrient.

53. The formulation of claim 52 wherein the plant micronutrient is selected from the group consisting of a boron compound, an iron compound, a magnesium compound, a manganese compound, a molybdenum compound, and a zinc compound.

54. A stable aqueous formulation, comprising:
- about 31% salicylic acid;
- about 16% hydrolyzed chitosan;
- about 11% potassium hydroxide; and
- about 2% humic acid.

* * * * *